United States Patent [19]

Cagle et al.

[11] Patent Number: 5,149,693
[45] Date of Patent: Sep. 22, 1992

[54] COMBINATION OF TOBRAMYCIN AND FLUOROMETHOLONE FOR TOPICAL OPHTHALMIC USE

[75] Inventors: Gerald D. Cagle; Thomas O. McDonald; Allan L. Rosenthal, all of Fort Worth, Tex.

[73] Assignee: Alcon Laboratories, Inc., Fort Worth, Tex.

[21] Appl. No.: 440,912

[22] Filed: Nov. 22, 1989

Related U.S. Application Data

[63] Continuation of Ser. No. 165,952, Mar. 9, 1988, abandoned.

[51] Int. Cl.$^5$ .............................................. A61K 31/70
[52] U.S. Cl. ...................................... 514/40; 514/912
[58] Field of Search ................................. 514/40, 912

[56] References Cited

U.S. PATENT DOCUMENTS

| | | | |
|---|---|---|---|
| 4,407,792 | 10/1983 | Schoenwald et al. | 514/40 |
| 4,474,753 | 10/1984 | Haslam et al. | 424/78 |
| 4,478,822 | 10/1984 | Haslam et al. | 424/78 |
| 4,668,506 | 5/1987 | Bawa | 424/429 |

OTHER PUBLICATIONS

*Physicians' Desk Reference for Ophthalmology*, "MAXIDEX", pp. 81-82 (1989).
*Physicians' Desk Reference for Ophthalmology*, "MAXITROL", pp. 82-83 (1989).
*Physicians' Desk Reference for Ophthalmology*, "TOBREX", p. 88 (1989).
*Physicians' Desk Reference for Ophthalmology*, "FML", pp. 95-97 (1989).
*Physicians' Desk Reference for Ophthalmology*, "CORTISPORIN", pp. 116-117 (1989).
*Physicians' Desk Reference for Ophthalmology*, "NEODECADRON", pp. 144-145 (1989).
Schoenwald, R. D., et al., "Ophthalmic Bioequivalence of Steroid/Antibiotic Combination Formulations", *Biological Abstracts*, vol. 85, 1988, Abstract No. 41064.
Unlisted Drugs, vol. 40, No. 11, Nov. 1988, p. 218, Abstract B: "Tobradex".
Stewart, R. S., et al., "Efficacy and Safety of Tobramycin-Dexamethasone Ophthalmic Suspension Tobradex in Prevention of Infection and Reduction of Inflammation Following Cataract Surgery", *Biological Abstracts*, Abstract No. 86086941.
Schoenwald, R. D., et al., "Ophthalmic Bioequivalence of Steroid/Antibiotic Combination Formulations", *Biopharmaceutics & Drug Disposition*, vol. 8, 1987, pp. 527-548.

*Primary Examiner*—Ronald W. Griffin
*Assistant Examiner*—Pamela S. Webber
*Attorney, Agent, or Firm*—James A. Arno; Gregg C. Brown

[57] ABSTRACT

Disclosed are pharmaceutical compositions comprising tobramycin and fluorometholone or fluorometholone acetate for topical ophthalmic delivery and methods of treatment comprising administering said composition when indicated for infection and control of inflammatory response for optimal wound healing and normalization of the eye.

5 Claims, No Drawings

COMBINATION OF TOBRAMYCIN AND FLUOROMETHOLONE FOR TOPICAL OPHTHALMIC USE

This is a continuation of application Ser. No. 07/165,952, filed Mar. 9, 1988, now abandoned.

BACKGROUND OF THE INVENTION

This invention relates to the topical ophthalmic use of antibiotics in combination with anti-inflammatory steroids for treating ophthalmic infections and attendant inflammation. Such combinations or formulations are available in the ophthalmic art. However, there are concerns and expressed reservations in the ophthalmic community about the safety and efficacy of such prior art combinations. There is, moreover, a long felt need for an effective and safe topical ophthalmic pharmaceutical composition of a potent steroid and a broad spectrum antibiotic which, when administered to the eye when indicated for bacterial infection or as a prophylactic after ophthalmic trauma and injury, will not, as a possible expression of the steroid component, inhibit the activity of the antibiotic nor interfere with normal wound healing, but at the same time will control inflammation. Unexpectedly it has been discovered that the broad spectrum aminoglycoside antibiotic tobramycin in combination with the potent steroid fluorometholone or its acetate meets these criteria.

DETAILED DESCRIPTION OF THE INVENTION

The compositions of the present invention are administered topically. The dosage range is 0.001 to 5.0 mg/per eye; wherein the cited mass figures represent the sum of the two components, fluorometholone or its acetate and tobramycin. Fluorometholone acetate is preferred. The compositions of the present invention can be administered as solutions, suspensions, or emulsions (dispersions) in a suitable ophthalmic vehicle.

In forming compositions for topical administration, the mixtures are preferably formulated as 0.01 to 2.0 percent by weight solutions in water at a pH of 4.5 to 8.0 (figures relate to combined presence of tobramycin and fluorometholone or fluorometholone acetate). While the precise regimen is left to the discretion of the clinician, it is recommended that the resulting solution be topically applied by placing one drop in each eye two times a day.

Other ingredients which may be desirable to use in the ophthalmic preparations of the present invention include preservatives, co-solvents and viscosity builder agents.

Antimicrobial Preservative

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium sorbic acid, Onamer M, or other agents known to those skilled in the art. Typically such preservatives are employed at a level of from 0.001% to 1.0% by weight.

Co-Solvents

The solubility of the components of the present compositions may be enhanced by a surfactant or other appropriate co-solvent in the composition. Such co-solvents include polysorbate 20, 60, and 80, Pluronic F-68, F-84 and P-103, cyclodextrin, or other agents known to those skilled in the art. Typically such co-solvents are employed at a level of from 0.01% to 2% by weight.

Viscosity Agents

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity builder agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The following example are representative pharmaceutical compositions of the invention for topical use when indicated against inflammation and infection.

EXAMPLE I

| | | |
|---|---|---|
| Fluorometholone Acetate, USP | 1.0 mg + 5% excess | 0.10% + 5% excess |
| Tobramycin, USP | 3.0 mg + 5% excess | 0.30 + 5% excess |
| Benzalkonium Chloride Solution (10%), NF | 0.001 ml + 10% excess | 0.10% + 10% excess[1] |
| Edetate Disodium, USP | 0.1 mg | 0.01% |
| Sodium Chloride, USP | 3.0 mg | 0.3% |
| Sodium Sulfate, USP | 12.0 mg | 1.2% |
| Tyloxapol, USP | 0.5 mg | 0.05% |
| Hydroxyethylcellulose | 2.5 mg | 0.25% |
| Sulfuric Acid and/or Sodium Hydroxide, NF | QS for pH adjustment to 5.5 ± 0.5 | |
| Purified Water, USP | QS to 1 ml | QS to 100% |

[1]The benzalkonium chloride, NF concentration is equivalent to 0.01% (+10% excess).

EXAMPLE II

| | | |
|---|---|---|
| Fluorometholone Acetate, USP | 0.1% + 2% excess | 1 mg + 2% excess |
| Tobramycin, Micronized, USP | 0.3% + 7% excess | 3 mg + 7% excess |
| Chlorobutanol, Anhydrous, NF | 0.5% + 25% excess | 5 mg + 15% excess |
| Mineral Oil, USP | 5% | 50 mg |
| White Petrolatum, USP | QS 100% | QS 1 g |

The invention has been described herein by reference to certain preferred embodiments. However, as obvious variations thereon will become apparent to those skilled in the art, the invention is not to be considered as limited thereto.

What is claimed is:

1. A method of treating ophthalmic inflammation and infection which comprises administering topically to the affected eye of a human host a therapeutically effective amount of an ophthalmic pharmaceutical composition comprising an anti-inflammatory effective amount of a steroid selected from the group consisting of fluorometholone and fluorometholone acetate; an anti-infective effective amount of tobramycin; and a pharmaceutically acceptable carrier therefor.

2. A method according to claim 1, wherein the steroid comprises fluorometholone acetate.

3. A method according to claim 1, wherein the ratio of the tobramycin to the steroid is in the range of from 0.1:1.0 to 10.0:1.0.

4. A method according to claim 3, wherein the composition is an aqueous solution; the combined concentration of the tobramycin and the steroid is in the range of 0.01 to 2.0 percent by weight; and the pH of the solution is in the range of 4.5 to 8.0.

5. A method according to claim 4, wherein the steroid comprises fluorometholone acetate.

* * * * *